(12) United States Patent
Machy et al.

(10) Patent No.: US 6,991,648 B2
(45) Date of Patent: Jan. 31, 2006

(54) VASCULAR PROSTHESIS IMPREGNATED WITH CROSSLINKED DEXTRAN

(75) Inventors: Delphine Machy, Eragny sur Oise (FR); Jacqueline Jozefonvicz, Lamorlaye (FR); Didier Letourneur, Le Plessis Robinson (FR)

(73) Assignee: Therapeutiques Substitutives, Villetaneuse (FR)

( * ) Notice: Subject to any disclaimer, the term of this patent is extended or adjusted under 35 U.S.C. 154(b) by 235 days.

(21) Appl. No.: 10/240,989

(22) PCT Filed: Mar. 30, 2001

(86) PCT No.: PCT/FR01/00964

§ 371 (c)(1),
(2), (4) Date: Jan. 13, 2003

(87) PCT Pub. No.: WO01/76652

PCT Pub. Date: Oct. 18, 2001

(65) Prior Publication Data

US 2003/0163186 A1    Aug. 28, 2003

(30) Foreign Application Priority Data

Apr. 10, 2000  (FR)  .................... 00 04554

(51) Int. Cl.
*A61F 2/06* (2006.01)

(52) U.S. Cl. ..................................... 623/1.45; 623/1.1

(58) Field of Classification Search ................ 623/1.1, 623/1.36, 1.38, 1.39, 1.42–1.49, 2.42
See application file for complete search history.

(56) References Cited

U.S. PATENT DOCUMENTS

| 4,740,594 | A | 4/1988 | Mauzac et al. |
| 4,808,709 | A | 2/1989 | Onishi |
| 5,415,619 | A | 5/1995 | Lee et al. |
| 5,693,625 | A | 12/1997 | Barritault et al. |
| 6,379,382 | B1 * | 4/2002 | Yang .......................... 623/1.42 |
| 6,410,519 | B1 * | 6/2002 | Gruskin et al. ................ 514/59 |

FOREIGN PATENT DOCUMENTS

WO    WO 00/02596    1/2000

* cited by examiner

*Primary Examiner*—Corrine McDermott
*Assistant Examiner*—William H Matthews
(74) *Attorney, Agent, or Firm*—Alston & Bird LLP

(57) ABSTRACT

The invention concerns a flexible vascular prosthesis comprising a synthetic support impregnated with at least a covalently crosslinked dextran and/or at least a functionalised derivative of covalently crosslinked dextran. The invention also concerns a method for preparing said prosthesis.

11 Claims, 2 Drawing Sheets

VASCULAR PROSTHESIS IMPREGNATED WITH CROSSLINKED DEXTRAN

Figure 1:
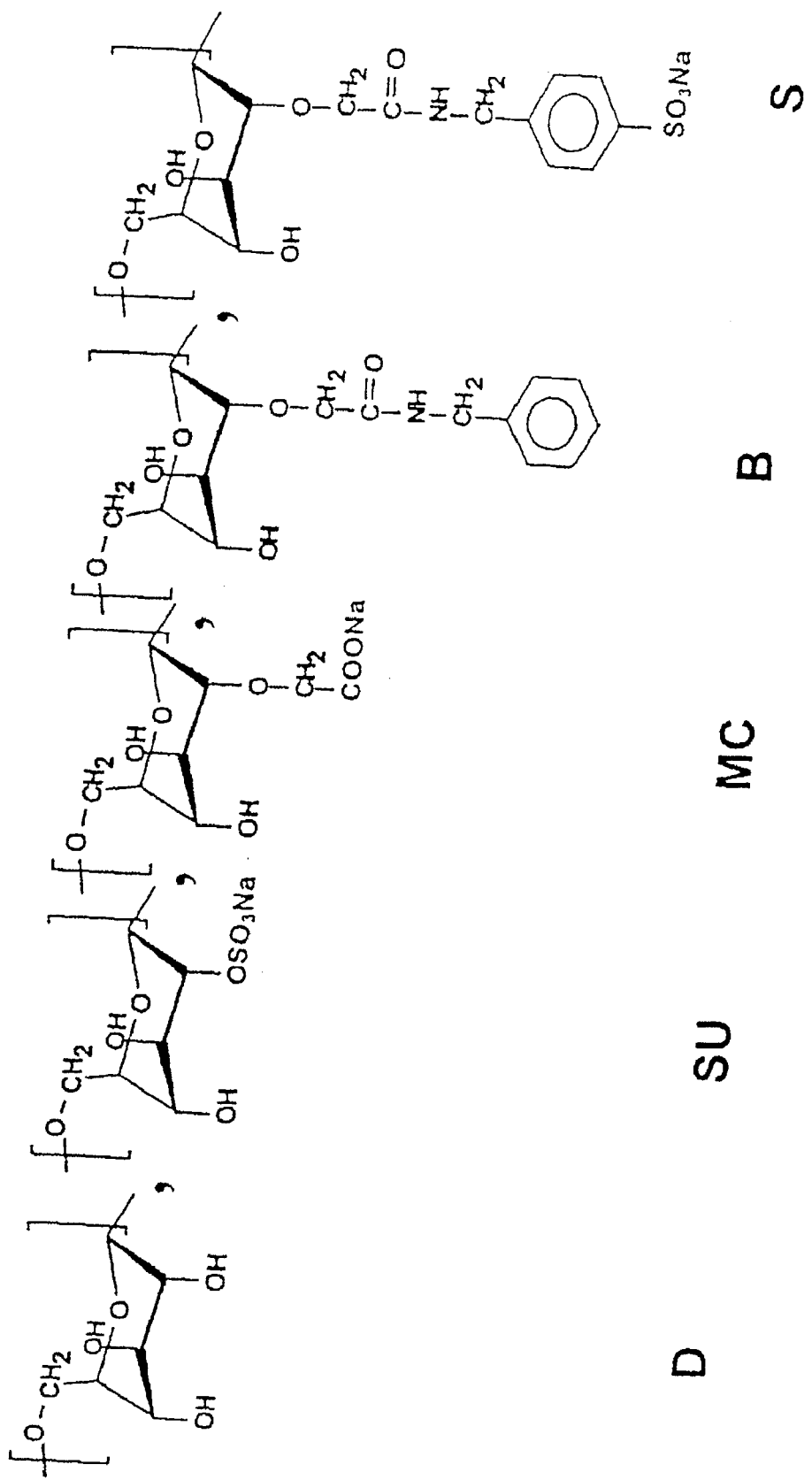

The present invention relates to a vascular prosthesis impregnated with crosslinked dextran and/or with a functionalized derivative of crosslinked dextran, and also to a process for preparing such a prosthesis.

In reparative vascular surgery, the use of synthetic substitutes, such as prostheses made of polyester, nylon, polypropylene, polyacrylonitrile, polyurethane, polyetherurethane, polyethylene terephthalate or expanded polytetrafluoroethylene, is an alternative to biological grafting.

To make these synthetic substitutes biocompatible and, in the case where the substitutes are not in themselves impermeable, to impart impermeability properties, their surface may be coated with biological substances, such as plasma proteins (albumin or fibrin) or extracellular matrix proteins (collagen, gelatin or fibronectin).

However, these proteins have the drawback of being derived from animal or human sources, resulting in a potential risk of contamination with pathogens and toxins.

It has already been proposed to coat the surface of these synthetic substitutes with optionally carboxymethylated alginate (patent U.S. Pat. No. 5,415,619). However, rapid clotting of blood at the surface of the prosthesis and a substantial inflammatory response after implanting this type of prosthesis are observed.

A device that is compatible with the blood medium, comprising a polymeric base material and a substantially nonionic water-soluble polymer directly attached to the surface of said base material, this water-soluble polymer possibly being chosen from polymers of the type such as acrylamide or methacrylamide; polyvinylpyrrolidone; partially or totally saponified polyvinyl alcohols; polyethylene glycol and noncrosslinked dextran, has also already been proposed, especially in patent U.S. Pat. No. 4,743,258. However, the use of such polymers as vascular prosthesis coatings is unsatisfactory since they are rapidly released into the blood circulation, owing to their solubility in aqueous medium, thus resulting in the removal of the coating from the prosthesis.

Moreover, pretreatments may be performed with the patient's blood, before implanting the prosthesis. However, these methods are limited since they require the patient to undergo transfusions, which take time and cannot be undertaken in the event of an emergency. In addition, they cannot be used when the patients are under anticoagulant treatment, which is often the case.

The Applicant thus sets itself the aim of overcoming the drawbacks of the prior art and of providing a vascular prosthesis coated with a substance that is not of animal origin, the resulting prosthesis being both impermeable and flexible. In addition, the prosthesis bearing its coating must be nontoxic and nonthrombogenic, and must not trigger an inflammatory reaction when it is implanted in vivo, while at the same time retaining its integrity after implantation.

One subject of the present invention is thus a flexible vascular prosthesis, characterized in that it comprises a synthetic support impregnated with at least one covalently crosslinked dextran and/or with at least one covalently crosslinked functionalized dextran derivative.

For the purposes of the present invention, the term "flexible" means a prosthesis that can be easily manipulated by the surgeon during implantation, and that is flexible enough to easily withstand folding and twisting without the tubular shape of the prosthesis giving way and without the walls becoming stuck to each other.

Dextran may be defined as a polysaccharide consisting of a sequence of α-D-glucopyranose units linked together via α(1–6) bonds.

The synthetic support used in the prosthesis according to the present invention consists, for example, of polyester, nylon, polypropylene, polyacrylonitrile, polyurethane, polyetherurethane, polyethylene terephthalate (woven or knitted) or expanded polytetrafluoroethylene.

The flexible vascular prosthesis according to the invention has the advantage of being impermeable with regard to the presence of the crosslinked dextran, and biocompatible (that is to say that it does not trigger an unfavorable biological response in the receiving individual) owing to the presence of the functionalized derivative of crosslinked dextran. It is suitable for sterilization with gamma radiation or with ethylene oxide, these treatments having no adverse effect on its impermeability or on its flexibility. It also has the advantage of maintaining constant chemical and physicochemical characteristics after a permanent contact, for 24 hours, of the prosthesis in a flow of water in a closed circuit, so as to reproduce the conditions of implantation in the blood circulation. Under these conditions, the amount of dextran released reaches a plateau that represents less than 1% by weight only of the dextran used to coat the prosthesis.

The use of dextran and/or of functionalized derivatives of dextran to coat the prosthetic support avoids any risk of contamination with animal pathogens. In addition, the prosthesis in accordance with the present invention has the advantage of not being thrombogenic (it does not activate the clotting system) and of not triggering any inflammatory reaction in the receiving individual.

Functionalized derivatives of dextran that may be used to impregnate the vascular prosthesis according to the present invention are, for example, those described in the international PCT patent application published under the number WO 99/29734 or in the article by D. Logeart-Avramoglou and J. Jozefonvicz published in *J. Biomed. Mater. Res.* (*Appl. Biomater.*) 48, 578–590, 1999.

Such derivatives, the preparation of which is described in international PCT patent application WO 99/29734, correspond, for example, to the general formula $DMC_aB_bSu_cS_d$ in which:

D represents a polysaccharide chain consisting of sequences of α-D-glucopyranose units linked together via α(1–6) bonds, MC represents methylcarboxylate groups, B represents carboxymethylbenzylamide groups, Su represents sulfate groups, S represents sulfonate groups, and a, b, c and d represent the degree of substitution (ds), expressed relative to the number of free hydroxyl functions in one glucoside unit of the dextran, with MC, B, Su and S groups respectively, a being equal to 0 or $\geq 0.2$, b being equal to 0 or $\geq 0.1$, c being equal to 0 or $\geq 0.1$ and d being equal to 0 or $\leq 0.15$, on condition that, when d=0, a and/or b are ≠0.

Among these functionalized dextran derivatives that may be used more particularly are those selected from the group consisting of:

functionalized dextrans in which $a \geq 0.5$, c is equal to 0 or $\leq 0.5$ and $d \leq 0.15$ or equal to 0 and in which the weight-average molar mass is between 3 000 and 5 000 000 g/mol, functionalized dextrans in which $a \geq 0.3$, c is equal to 0 or $\leq 0.4$ and $d \leq 0.15$ or equal to 0 and in which the weight-average molar mass is between 3 000 and 5 000 000 g/mol, functionalized dextrans in which a≧0.5, c is equal to 0 or ≦0.4 and d≦0.15 or equal to 0 and in which the weight-average molar mass is between 3 000 and 5 000 000 g/mol, and functionalized dextrans in which a≧0.2, c≧0.3 and d≦0.15 or equal to 0 and in which the weight-average molar mass is between 3 000 and 5 000 000 g/mol.

As additional examples of functionalized dextran derivatives that may be used to impregnate the vascular prosthesis according to the present invention, mention may also be made of:

1) the dextran derivatives described in European patent 0 146 455, which comprise, randomly:
at least 35% approximately of units B consisting of saccharide units A substituted with radicals containing a carboxyl function corresponding to the structure —O—(CH$_2$)$_n$—R—COO$^-$ in which R represents a single bond or a group —CO—NH—(CH$_2$)$_{n'}$—, n being a number between 1 and 10 and n' being between 1 and 7,
at least 3% approximately of units D, i.e. of saccharide units A substituted with a chain comprising a group of structure:

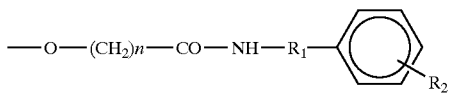

in which n is as defined above, R$_2$ represents an anion of a physiologically acceptable mineral or organic salt, and R$_1$ represents a single bond, a —CH$_2$— group or a group:

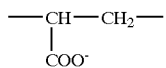

optionally, unsubstituted saccharide units A and/or units C consisting of units A substituted with radicals of the following structure, in which R$_1$ and n are as defined above:

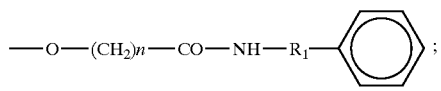

2) the dextran derivatives described in European patent 0 428 182, which comprise units A and C and at least 35% of units B, these units being as defined above in relation with European patent 0 146 455.

According to one advantageous embodiment of the vascular prostheses in accordance with the present invention, the weight ratio between the functionalized dextran derivative and the dextran is between 1/99 and 30/70, preferably between 3/97 and 7/93 and even more preferably equal to 5/95 approximately.

According to another advantageous embodiment of the vascular prostheses in accordance with the present invention, said synthetic support is also impregnated with at least one covalently crosslinked natural or synthetic polysaccharide functionalized at least with carboxylate and/or sulfate functions. An example of such a functionalized polysaccharide is heparin.

The weight ratio between the functionalized polysaccharide and the dextran is advantageously between 1/99 and 30/70 and preferably between 1/99 and 20/80.

When the vascular prosthesis in accordance with the present invention comprises both a functionalized dextran derivative and a functionalized polysaccharide, the weight ratio between the functionalized dextran derivative and the functionalized polysaccharide is advantageously between 1/99 and 99/1.

When functionalized dextran derivatives and/or natural or synthetic polysaccharides functionalized with at least carboxylate and/or sulfate functions, as defined above, are present in the prosthesis in accordance with the invention, they give said prosthesis specific biological activities.

In particular, the presence of functionalized dextran derivatives gives the prosthesis in accordance with the present invention the possibility of developing specific interactions with the biological medium into which it is implanted; a proliferation of human endothelial cells into the prosthesis is especially observed, this process promoting the integration of the graft into the biological medium.

In addition, depending on their degrees of substitution with various functionalized groups, the functionalized dextran derivatives and the functionalized polysaccharides described above may have cicatrizing properties, anticomplement activity and blood-plasma-substitute activity, modulatory activity of cell proliferation or anticoagulant properties.

A subject of the present invention is also a process for preparing a vascular prosthesis as described above, characterized in that it comprises the following steps:

a) preparation of a solution of at least one dextran and/or of at least one functionalized dextran derivative, b) impregnation of the synthetic support using this solution, c) crosslinking of said dextran and/or of said functionalized dextran derivative.

The solution prepared during step a) may consist of an aqueous solution, conventionally based on osmosed water. It comprises, for example, between 1% and 70% (m/V) of dextran, or between 1% and 70% (m/V) of functionalized dextran derivative, or between 1% and 70% (m/V) of dextran and of functionalized dextran derivative, depending on the type of dextran used and on its weight-average molar mass.

The dextran used in the process according to the invention preferably has a weight-average molar mass of between 10 000 and 50 000 000 g/mol.

Examples that may be mentioned include the dextrans T40, T70 and T500, with weight-average molar masses respectively equal to about 40 000, 70 000 and 460 000 g/mol, sold by the company Pharmacia Biotech, and the dextran 5M with a weight-average molar mass equal to or greater than 5×10$^6$ g/mol, sold by the company Sigma. Depending on the type of dextran used, the solution prepared during step a) of the process according to the present invention comprises, for example, from 20% to 70% (m/V) of dextran T40, from 10% to 70% (m/V) of dextran T70, from 10% to 50% (m/V) of dextran T500, or from 1% to 15% (m/V) of dextran 5M.

According to one advantageous embodiment of the process in accordance with the present invention, this process comprises, between steps a) and b), the addition to the solution prepared during step a) of a crosslinking agent, for example STMP (sodium trimetaphosphate), phosphorus oxychloride ($POCl_3$), epichlorohydrin, formaldehydes, carbodiimides, glutaraldehydes or any other compound that is suitable for crosslinking a polysaccharide.

In this embodiment, steps b) and c) are advantageously carried out simultaneously at a pH of between 3 and 10, at a temperature of between 10 and 40° C. approximately and for a time of less than or equal to 150 minutes approximately.

According to another advantageous embodiment of the process in accordance with the present invention, this process comprises, between steps b) and c), a step of drying the support, followed by a step of impregnating the support with a solution, in at least one organic solvent (such as ether), of a crosslinking agent.

A crosslinking agent that is suitable is, for example, a carbodiimide or BDGE (1,4-butanediol diglycidyl ether), this crosslinking agent possibly being used in a proportion of 10 to 30 mol % per 100 mol of glucoside units in the polysaccharide (functionalized or unfunctionalized dextran), or any other crosslinking agent that is soluble in an organic solvent.

In this embodiment, steps b) and c) are each advantageously carried out at a pH of between 3 and 10 and at a temperature of between 10 and 40° C. approximately, step b) advantageously being carried out for a time of less than or equal to 150 minutes approximately and step c) for a time of between 15 minutes and 18 hours approximately.

According to one advantageous arrangement of this embodiment, said successive steps of preparing a solution of at least one dextran and/or of at least one functionalized dextran derivative, of impregnating the support with this solution, of drying the support, of impregnating the support with a solution, in at least one organic solvent, of a crosslinking agent, and of crosslinking said dextran and/or said functionalized dextran derivative are, after drying the support, repeated at least once, preferably two to three times.

According to another advantageous embodiment of the process in accordance with the present invention, step c) of crosslinking the dextran and/or the functionalized dextran derivative is followed by a step of washing the prosthesis, for example using a mixture of osmosed water and of softeners and/or plasticizers as will be described below.

According to another advantageous embodiment of the process in accordance with the present invention, said solution of at least one dextran and/or of at least one functionalized dextran derivative prepared during step a) also comprises at least one natural or synthetic polysaccharide functionalized at least with carboxylate and/or sulfate functions.

Such polysaccharides are as described previously in relation with the flexible vascular prosthesis in accordance with the present invention.

According to yet another advantageous embodiment of the process in accordance with the present invention, said solution of at least one dextran and/or of at least one functionalized dextran derivative prepared during step a) also comprises at least one additive chosen from plasticizers and softeners and/or one or more active principles selected from the group consisting of anticoagulants (such as anti-vitamin K or aspirin), antibacterial agents and anti-infectious agents. Said active principles may, for example, be present in said aqueous solution in a proportion of from 1% to 10% by weight relative to the polysaccharides used.

Examples of plasticizers that may be used include glycerol or mannitol, which are present, for example, in a proportion of from 1% to 10% by volume.

Examples of softeners that may be used include lactic acid, ascorbic acid, ethylene glycol, propylene glycol and sorbitol, which are present, for example, in a proportion of from 0.1% to 5% by volume.

Examples of antibacterial agents and of anti-infectious agents that may be used are, in a nonlimiting manner, rifampicin, minocycline, chlorhexidine, silver ion agents and silver-based compositions.

A subject of the present invention is also a flexible vascular prosthesis as defined above, characterized in that it may be obtained by the process according to the invention as defined above.

Figure 2:
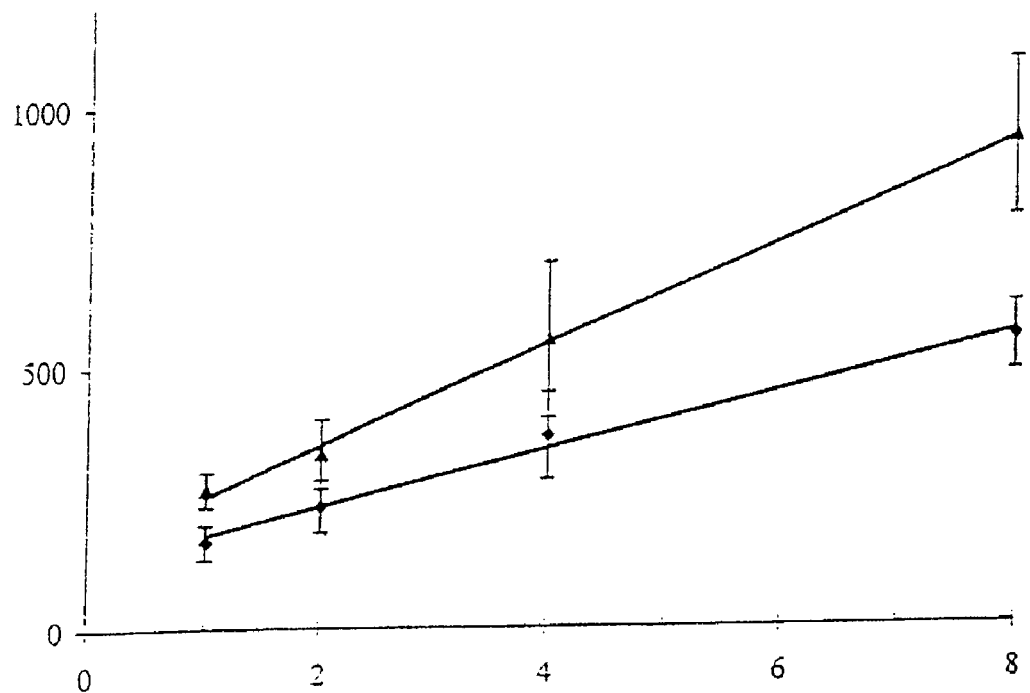

In addition to the preceding arrangements, the invention also comprises other arrangements that will emerge from the description that follows, which refers to examples of the preparation of vascular prostheses according to the present invention and for the evaluation of their cell biocompatibility, and also to the attached drawings, in which:

FIG. 1 diagrammatically shows the structure of a functionalized dextran derivative substituted with the various chemical groups MC, B, Su and S attached to the glucoside units D; by way of example, the position of the substituent on the various carbons of the glucoside units is presented on carbon 2; and FIG. 2 shows the growth curves of permanent human endothelial cells EA.hy 926 on samples of vascular prostheses according to the invention comprising either an unfunctionalized dextran derivative (curve -v-), or an unfunctionalized dextran derivative and a functionalized dextran derivative (curve -π-), the time (in days) given on the x-axes and the number of cells per $cm^2$ (×10) on the y-axes.

It should be clearly understood, however, that these examples are given solely as illustrations of the subject of the invention, of which they do not in any way constitute a limitation.

EXAMPLE 1

Preparation of Vascular Prostheses According to the Present Invention, Which Comprise a Synthetic Support Impregnated with a Dextran Crosslinked with BDGE 1) Synthetic support, dextran and crosslinking agent used The synthetic support used consists of knitted polyethylene terephthalate (PET), supplied by the company Cardial & Bard under the trade name "Dialine I". Its water permeability is 1010 ml/min/$cm^2$ according to ISO/DIS standard 7198:1996. It is in the form of a ribbed textile 40 to 60 cm long (in stretched form) and 8 to 10 mm in diameter. Samples 20 cm long (stretched) are used in the context of the present example.

The dextran used is dextran 5M with a weight-average molar mass equal to $5 \times 10^6$ g/mol, sold by the company Sigma.

As regards the dextran-crosslinking agent, it is BDGE (1,4-butanediol diglycidyl ether, Aldrich).

2) Protocol

The protocol for preparing the vascular prostheses consists of series of successive cycles of impregnating the PET synthetic support with a dextran solution and of crosslinking in an organic solvent, separated by drying steps.

The dextran solutions prepared for the impregnation steps are solutions containing 9%, 9.5% and 10% (m/V) of 5M dextran in osmosed water. To these solutions are added lactic acid (0.7% by volume) and glycerol (2% by volume). The pH is adjusted to 7 using a 2M sodium hydroxide solution.

The PET synthetic support is impregnated using a peristaltic pump which draws the dextran solution and entrains it inside the tubular sample, via its two ends. The impregnation time is from about 10 seconds to 5 minutes.

The impregnation is followed by drying the samples in an oven at 40° C. for 24 hours.

A step of crosslinking the dextran is then performed: the samples are placed in an ether solution, to which is added the BDGE (22.3 mol per 100 mol of glucoside units of the dextran). The crosslinking is carried out for 18 hours.

The samples are then dried for one hour under a suction hood.

Three successive cycles of impregnation and crosslinking are carried out, then the samples are washed three times for three hours using a solution of osmosed water comprising 0.7% (V/V) of lactic acid and 2% of glycerol (V/V), of pH 7.

3) Results

For each sample, the degree of coating of the sample R (%) is measured, which corresponds to the increase in the mass of the sample after its treatment with the polysaccharide solution ($R=(P_2-P_1)/P_1 \times 100$, $P_1$ representing the initial mass of the sample and $P_2$ its final mass after treatment).

The static permeability of the samples is also measured according to ISO/DIS standard 7198:1996, which consists in measuring the flow rate of water passing through a given area of a sampled prosthesis, by gravimetry and under hydrostatic pressure. The sample may be immersed in pure water at ambient temperature in order to impregnate it with water before carrying out the test ("Hyd permeability": permeability in the hydrated state), or may be subjected directly to the test ("Unhyd permeability": permeability in the unhydrated state). The permeability is the quotient of the flow rate of water (in ml/min) per unit area (in $cm^2$): it is expressed in $ml/min/cm^2$. In the examples that follow, except where otherwise mentioned, the permeabilities measured are static permeabilities obtained according to ISO/DIS standard 7198:1996.

The results obtained for prostheses 1 to 3 are collated in Table I.

TABLE I

| Prosthesis No. | Dextran concentration of the impregnation solution (m/V) | R (%) | Unhyd permeability | Hyd permeability |
|---|---|---|---|---|
| 1 | 9% | 24 ± 2 | 54 | 1.5 |
| 2 | 9.5% | 22 ± 3 | 50 | 1 |
| 3 | 10% | 27 ± 1 | 14 | 1 |

Prostheses 1 to 3 have the required flexibility nature and degrees of coating to produce good sealing while at the same time maintaining flexibility of the sample.

EXAMPLE 2

Another Example of the Preparation of Vascular Prostheses According to the Present Invention, Which Comprise a Synthetic Support Impregnated with a Dextran Crosslinked Using BDGE The synthetic support, the dextran and the crosslinking agent used are as described in Example 1. In contrast with Example 1, the protocol followed comprises only two successive cycles of impregnation and crosslinking, with three 3-hour washes at the end of the protocol. The impregnation solutions consist of 5M dextran at a concentration of 10% (m/V), without glycerol or lactic acid during the first cycle and with 2% by volume of glycerol for the second cycle. The BDGE concentration, which is identical for the two cycles, is 15%, 18% or 20% (in terms of number of moles relative to 100 mol of glucoside units of the dextran) according to the samples.

The results obtained for prostheses 4 to 6, which have the required flexibility nature, are collated in Table II.

TABLE II

| Prosthesis No. | Amount of BDGE (mol %) | R (%) | Unhyd permeability | Hyd permeability |
|---|---|---|---|---|
| 4 | 20% | 27 ± 1 | 2 | 1 |
| 5 | 18% | 26 ± 0.5 | 14 | 5 |
| 6 | 15% | 25.5 ± 1 | 20 | 6 |

EXAMPLE 3

Preparation of Vascular Prostheses According to the Present Invention, Which Comprise a Synthetic Support Impregnated with a Dextran Crosslinked with STMP, and also Optionally a Functionalized Polysaccharide 1) Synthetic support, dextrans and crosslinking agent used The synthetic support (knitted PET) and the dextran (5M dextran) used are identical to those described in Example 1. The crosslinking agent consists of STMP (sodium trimetaphosphate, sold by Sigma).

The functionalized dextran derivative used, with a weight-average molar mass of about 106 900 g/mol, is $DMC_3B_2$; it corresponds to the general formula $DMC_bB_b$-$Su_cS_d$ as described above, in which the degree of substitution with methylcarboxylate groups (index a) is equal to 0.87 and the degree of substitution with carboxymethylbenzylamide groups (index b) is equal to 0.26, the indices c and d being equal to 0. Its preparation protocol is as described in the European patent published under No. 0 146 455.

2) Protocol

A 5M solution of dextran at 10% (m/V) is prepared in 0.2M sodium hydroxide in the presence of 0.7% (by volume) of lactic acid and 2% (by volume) of glycerol. This solution may also comprise, if necessary, the functionalized dextran derivative $DMC_3B_2$; in which case, the 5M dextran is mixed, in the solid phase, with the dextran $DMC_3B_2$ before being dissolved, the proportion of $DMC_3B_2$ being equal to 3% by weight relative to the weight of the 5M dextran, i.e. a weight ratio of 3/97 between the functionalized dextran derivative and the 5M dextran.

As a variant, the dextran solution may also comprise heparin (anticoagulant) in a proportion of 1%, 3%, 5% or 10% by weight relative to the weight of the 5M dextran, or weight ratios between the heparin and the dextran of 1/99, 3/97, 5/95 and 10/90, respectively.

The impregnation solution thus prepared is at 40° C. for 20 minutes and the STMP (8 mol per 100 mol of glucoside units of the 5M dextran and of the $DMC_3B_2$ dextran, if the latter is present), prediluted in 0.5 ml of 0.2M sodium hydroxide, is then added to the impregnation solution.

The synthetic support is impregnated with this solution in the same manner as described in Example 1, at ambient temperature and for 10 seconds to 5 minutes. If the $DMC_3B_2$ dextran is present, it will be "cocrosslinked" with the 5M dextran.

The prosthesis is dried for 2 hours at 40° C., and then washed three times, for 3 hours, using a solution of osmosed water comprising 0.7% (V/V) of lactic acid and 2% of glycerol (V/V), of pH 7.

3) Results

The results obtained for prostheses 7 to 12 are collated in Table III; the parameters regarding the of coating R and the permeabilities are measured as indicated in Example 1.

TABLE III

| Prosthesis No. | Composition of the coating | Unhyd permeability | Hyd permeability |
|---|---|---|---|
| 7 | 5M dextran | 0 | 0 |
| 8 | 5M dextran + $DMC_3B_2$ | 0 | 0 |
| 9 | 5M dextran + heparin (1%) | 3.3 | 0 |
| 10 | 5M dextran + heparin (3%) | 10 | 0 |
| 11 | 5M dextran + heparin (5%) | 30 | 0 |
| 12 | 5M dextran + heparin (10%) | 40 | 0 |

Prostheses 7 to 12 are flexible. The presence functionalized dextran derivative $DMC_3B_2$ or of heparin does not disrupt the crosslinking reaction, the permeabilities in the hydrated state being identical in samples 7 to 12.

EXAMPLE 4

Another Example of the Preparation of Vascular Prostheses According to the Present Invention, Which Comprise a Synthetic Support Impregnated with a Dextran Crosslinked with STMP The synthetic support (knitted PET) and the crosslinking agent (STMP) are identical to those used in Example 3. The dextran used is T500, with a weight-average molar mass equal to 460 000 g/mol, sold by the company Pharmacia Biotech.

The process is performed in the same manner as in Example 3, the impregnation solution comprising 22% (m/V) of T500 dextran, 0.7% (by volume) of lactic acid and 2% (by volume) of glycerol. The STMP is present in a proportion of 8% (on a molar basis per 100 mol of glucoside units of the dextran).

Prosthesis sample 13 is obtained, which has the required flexibility and impermeability properties and whose characteristics are collated in Table IV:

TABLE IV

| Prosthesis No. | Composition of the coating | R (%) | Unhyd permeability | Hyd permeability |
|---|---|---|---|---|
| 13 | T500 dextran | 27 ± 1 | 1.5 | 0.5 |

EXAMPLE 5

Other Examples of the Preparation of Vascular Prostheses According to the Present Invention, Which Comprise a Synthetic Support Impregnated with a Dextran Crosslinked with STMP The synthetic support (knitted PET), the crosslinking agent(STMP) and the dextrans (T500 or 5M) used are identical to those described in Examples 3 and 4.

The process is performed in the same manner as in Example 3, the impregnation solution comprising either 20% (m/V) of T500 dextran, or 10% (m/V) of 5M dextran, and also 0.7% (by volume) of lactic acid and 2% (by volume) of glycerol. The STMP is present in a proportion of 8% (on a molar basis per 100 mol of glucoside units of the dextran).

The contact time, i.e. the time interval separating the addition of the STMP to the dextran solution and the impregnation of the sample with this solution, is varied.

Prosthesis samples 14 to 19 are obtained, which the required flexibility and impermeability properties, and whose characteristics are collated in Table V:

TABLE V

| Prosthesis No. | Composition of the coating | Contact time (minutes) | R (%) | Unhyd permeability | Hyd permeability |
|---|---|---|---|---|---|
| 14 | T500 dextran | 2 | 31 ± 1.0 | 1 | 0 |
| 15 | T500 dextran | 15 | 33 ± 1.5 | 0 | 0 |
| 16 | T500 dextran | 30 | 43 ± 1.0 | 0 | 0 |
| 17 | 5M dextran | 15 | 24 ± 1.5 | 0.2 | 0 |
| 18 | 5M dextran | 30 | 25 ± 0.5 | 0 | 0 |
| 19 | 5M dextran | 45 | 25 ± 0.2 | 0 | 0 |

Flexible and impermeable vascular prostheses according to the present invention may thus be obtained by varying the contact time of the crosslinking agent the dextran solution, before impregnation of the synthetic support.

The dextran crosslinking reaction starts as soon as the crosslinking agent is placed in contact with the dextran solution, causing an increase in the viscosity of the impregnation solution. The impregnation of the prosthetic support must be performed at a stage at which the impregnation solution is neither too liquid (which would give too thin a coating) or too viscous (the prosthetic support would be difficult to impregnate). The contact times given as examples in Table V above are suitable for obtaining prostheses having the desired characteristics.

EXAMPLE 6

Sterilization of a Prosthesis According to the Present Invention with Gamma Radiation Prosthesis samples 7 prepared in Example 3 were sterilized with gamma radiation, at a dose of 25 kGray. The permeabilities of the sterilized prostheses were measured, as were those of identical unsterilized prostheses. The results are given in Table VI.

TABLE VI

| Type of coating | R (%) | Unhyd permeability | Hyd permeability |
|---|---|---|---|
| Nonsterile prosthesis | 25 | 0 | 0 |
| Sterile prosthesis | 25 | 0 | 0 |

The prostheses remain leaktight and flexible after sterilization with gamma rays. The gamma radiation does not appear to degrade the appearance of the prostheses coatings.

On the contrary, they probably have an effect similar to that of a crosslinking agent: they create free radicals capable of interacting between themselves and which can form covalent bonds.

EXAMPLE 7

Measurement of the Integral Water Permeability of the Vascular Prostheses According to the Present Invention 1) Nature of the prosthesis samples Prosthesis 7 prepared in Example 3 is used, which comprises 10% (m/V) of 5M dextran, and also a prosthesis 20 is used, prepared in accordance with Example 3 using 10% (m/V) of 5M dextran and 7% (expressed on a weight basis relative to the amount of 5M dextran) of $DMC_3B_2$, i.e. a weight ratio between the functionalized dextran derivative and the 5M dextran equal to 7/93. The crosslinking agent is STMP, present in the impregnation solution to a proportion of 8 mol % per 100 mol of glucoside units of the dextran.

2) Parameters measured

For prostheses 7 and 20, the following are measured:
the static permeability in the hydrated or unhydrated state (measured according to ISO/DIS standard 7198:1996 as presented in Example 1),
the integral water permeability, evaluated according to the standardized ISO procedure 7198. Table VII below shows the length of the sample (l, in cm), the volume of water recovered (V, in ml/min) and the integral permeability (P, in ml/min/$cm^2$),
the degree of coating R, measured as indicated in Example 1,
the percentage of relative humidity RH, this parameter having an influence on the flexibility of the sample. The sample is weighed in the dry state (after treatment in an oven at 40° C.) and in the humidified state (sample placed in a bell-jar at 80% humidity), the difference between these weighings, relative to the weight of the dry sample, giving the percentage of relative humidity RH.

3) Results

The characteristics of samples 7 and 20, which especially show the required flexibility and permeability properties, are collated in Table VII.

TABLE VII

| Prosthesis No. | Unhyd permeability | Hyd permeability | Integral permeability | | | R (%) | RH (%) |
|---|---|---|---|---|---|---|---|
| | | | l | V | P | | |
| 7 | 0 | 0 | 8.4 | 2.1 | 0.08 | 36 | 52 |
| 20 | 0.67 | 0 | 7.3 | 12 | 0.52 | 31 | 45 |

EXAMPLE 8

In vitro Cellular Biocompatibility of the Coating Agents for the Vascular Prostheses According to the Present Invention This example is directed toward studying the cytocompatibility of the dextran gels used as coating agents for the vascular prostheses in accordance with the invention.

I) Preparation of the dextran gels

The dextran gels are prepared in the following manner:
unfunctionalized dextran gel (gel A): a 10% solution of 5M dextran with a weight-average molar mass equal to $5 \times 10^6$ g/mol, sold by the company Sigma, in a sterile aqueous 0.2M NaOH solution containing 0.7% of lactic acid and 2% of glycerol (solution A) is prepared;
unfunctionalized dextran gel and functionalized dextran gel (gels B to D): 10% solutions of 5M dextran as described above and containing 3% (w/v) of functionalized dextran of formula $DMC_aB_bSu_cS_d$ relative to the weight of unfunctionalized dextran, in a sterile aqueous 0.2M NaOH solution containing 0.7% of lactic acid and 2% of glycerol (Solutions B to D), are prepared. The substitution indices a, b, c and d of the dextrans of formula $DMC_aB_bSu_cS_d$ used are given in Table VIII below:

TABLE VIII

| | Functionalized dextran used | | | | Molar mass in |
|---|---|---|---|---|---|
| Solutions | a | b | c | d | g/mol |
| B | 0.81 | 0.20 | 0.13 | 0 | 67 000 |
| C | 0.61 | 0.39 | 0 | 0 | 63 000 |
| D | 0.61 | 0.39 | 0.04 | 0 | 63 000 |

The dextran solutions A to D thus prepared are heated at 40° C. for 20 minutes, then the crosslinking agent (8 mol of STMP per 100 mol of glucoside units, as described above in Example 3), prediluted in 0.5 ml of 0.2M sodium hydroxide, is added to these dextran solutions.

The mixtures are then poured into 12-well culture plates at a rate of 150 µl per well. When the crosslinking reaction is complete, the gels thus obtained are washed three times with sterile PBS.

II) Study of the adhesion of endothelial cells EA.hy 926 to Gels A to D

Human endothelial cells EA.hy 926 are inoculated at a rate of $2 \times 10^6$ cells into 3 ml of DMEM culture medium containing 10% fetal calf serum (FCS) and 2 µCi/ml of tritiated proline (Amersham). After culturing for 24 hours at 37° C., the cells are detached using a trypsin solution, centrifuged at 1 200 rpm and then resuspended in a DMEM culture medium containing 10% FCS. The cells are then counted using a Malassez cell, diluted and inoculated onto the plates containing the dextran gels A to D, at a rate of 50 000 cells per well. The culture plates are then incubated at 37° C. for 3 hours.

At the end of the incubation period, the inoculated wells are rinsed twice with PBS in order to remove the cells that have not adhered to the dextran gels.

The adherent cells are then detached using a trypsin solution, and the cells of each well are then placed in a counting flask containing 5 ml of scintillation liquid (Optiphase® "Hisafe", Wallack).

The measurement of the radioactivity present in each flask is carried out using a scintillation counter (LKB) at a rate of four 1-minute counts per flask.

The percentage of adhesion of the cells to the gels B to D is determined relative to the radioactivity emitted in the control wells, i.e. the wells containing the unfunctionalized dextran gel A.

The results obtained are given in Table IX below:

TABLE IX

| Gels | % of adhesion of the cells relative to the adhesion observed on gel A |
|---|---|
| A | 100 |
| B | 165 ± 19.7 |

TABLE IX-continued

| Gels | % of adhesion of the cells relative to the adhesion observed on gel A |
|---|---|
| C | 184 ± 15.7 |
| D | 195.7 ± 6.3 |

These results show that the presence of a functionalized dextran derivative makes it possible to promote the adhesion of the endothelial cells.

Similar results were obtained by performing the same experiment on smooth muscle cells of rat (CMI).

III) Study of the proliferation of EA.hy 926 endothelial cells on the gels A and C Human endothelial cells EA.hy 926 are inoculated at a rate of 10 000 cells per cm$^2$ into DMEM culture medium containing 10% FCS, on the dextran gels A and C.

After culturing for 5 days, the cells are rinsed three times with PBS and are then detached with 500 µl of a trypsin solution and suspended in an Isotron electrolyte solution. The cells are then counted using a Coulter Counter® counting machine.

The results for the cell proliferation observed on gel C are expressed as a percentage of the cell proliferation observed on gel A and are given in Table X below:

TABLE X

| Gel | % of proliferation of the cells relative to the proliferation observed on gel A |
|---|---|
| A | 100 |
| C | 116.5 ± 0.43 |

These results show that the presence of a functionalized dextran derivative promotes the proliferation of the endothelial cells.

Similar results were obtained by performing the same experiment on smooth muscle cells of rat (CMI).

This set of results shows that the presence of a functionalized dextran derivative according to the present invention promotes the adhesion and proliferation of endothelial cells, which is an important property for promoting the integration into the biological medium of the vascular prosthesis that it coats.

EXAMPLE 9

In vitro Cellular Biocompatibility of the Vascular Prostheses According to the Present Invention 1) Protocol To analyze the cytocompatibility of prostheses 7 and 8 synthesized in Example 3 with human endothelial cells EA.hy 926, 1 cm$^2$ samples are cut out of the prostheses, sterilized with gamma radiation and introduced into 24-well culture plates. Sterile glass inserts are placed on the samples to prevent them from rolling up on themselves once immersed in the culture medium.

The prosthesis samples are kept for 24 hours in the culture medium, i.e. a sodium pyruvate-free DMEM medium comprising 4 500 mg/ml of glucose (GIBCO), supplemented with L-glutamine (2 mM), HAT (2% V/V) and 10% fetal calf serum (GIBCO), then the medium is aspirated and the samples are inoculated with the human endothelial cells EA.hy 926 at a density of 5×10$^4$ cells/cm$^2$, each sample being prepared in triplicate. The inoculated samples are placed in an incubator at 37° C., under a humid atmosphere containing 5% $CO_2$, under static conditions. The medium is renewed every two days.

The cell proliferation is observed each day for 8 days, using an inverse optical microscope. To this end, the samples are washed three times in PBS (nonsterile), fixed in 4% formaldehyde, washed a further three times in PBS, then stained with Coomassie blue (5%) and finally decolorized with 70% ethanol, such that only the cell membranes remain colored. Under the microscope, the cells appear blue on a colorless background.

2) Results

FIG. 2 shows the growth curves for the permanent human endothelial cells EA.hy 926 on the vascular prosthesis samples 7 (-v-curve) and 8 (-π-curve), the time (in days) being given on the x-axes and the number of cells per cm$^2$ (×10) on the y-axes.

A significant difference is noted between the growth of the cells on samples 7 and 8: when the $DMC_3B_2$ is present in the prosthesis coating, the number of cells is gradually larger as the days pass, indicating that the presence of the functionalized dextran derivative in the prosthesis improves the proliferation of the human endothelial cells EA.hy 926.

Similar results were obtained with other endothelial cell cultures, namely the endothelial cells of human umbilical cord vein and the endothelial cells of bovine aorta. It thus appears that, in general, the presence of a functionalized dextran derivative in the vascular prosthesis according to the present invention promotes the proliferation of endothelial cells, which is an important property for promoting the integration of the graft into the biological medium.

EXAMPLE 11

Study of the Stability of a Vascular Prosthesis in Accordance with the Invention Compared with that of a Vascular Prosthesis Coated with Noncrosslinked Dextran 1) Preparation of the vascular prostheses A vascular prosthesis in accordance with the invention was prepared according to the protocol described in Example 3 and using the support and the dextran described above in Example 1 and the crosslinking agent described in Example 3 above.

For comparative purposes, a vascular prosthesis not forming part of the invention was prepared under the same conditions, except that the crosslinking agent was not added to the dextran solution.

2) Study of the stability of the coating

The assembly used for this study consisted of a water bath thermostatically maintained at 37° C. and a pump for circulating a continuous flow of a solution inside a vascular prosthesis. The flow rate of the pump was set at 7×10$^{-5}$ m$^3$ per second so as to reproduce the conditions of the physiological flow rate of the arterial circulation.

Samples of the circulating solution are taken at regular intervals to quantify the amount of dextran released. The dextran released is assayed indirectly by colorimetric assay of the carbohydrates in concentrated sulfuric acid/phenol medium according to the method of Dubois et al. (Analytical Chemistry, 1956. 3 (28), 350–356), optionally after lyophilization and dilution of the circulating solution when the amounts of dextran released are extremely small.

The results obtained for the prosthesis in accordance with the invention (impregnated with crosslinked dextran) are given in Table XI below:

TABLE XI

| Time in hours | Amount of dextran released in μg (prosthesis in accordance with the invention) |
|---|---|
| 1 | 25 |
| 2 | 35 |
| 12 | 65 |
| 24 | 70 |

It was not possible to measure the amount of dextran released over time by the prosthesis not in accordance with the invention (impregnated with a noncrosslinked dextran) since the dextran was all released during the first washing of the prosthesis, i.e. even before placing said prosthesis in contact with the flow of water in the closed circuit. This release of dextran has the consequence of breaking down the sealing properties of the prosthesis.

In contrast, after circulation for 24 hours, the amount of dextran released by the vascular prosthesis in accordance with the invention, i.e. impregnated with a covalently crosslinked dextran, reaches a plateau at 70 μg representing about 0.014% of the total amount of dextran impregnating the prosthesis. This negligible amount is indicative of the very great chemical stability over time of the vascular prostheses in accordance with the invention.

As emerges from the foregoing text, the invention is not in any way limited to its modes of implementation, preparation or application that have just been described in greater detail; on the contrary, it encompasses all variants that may occur to a person skilled in the art, without departing from the context or scope of the present invention.

What is claimed is:

1. A flexible vascular prosthesis, comprising a synthetic support impregnated with at least one covalently crosslinked dextran and with at least one covalently crosslinked functionalized dextran derivative.

2. The prosthesis as claimed in claim 1, wherein the weight ratio between the functionalized dextran derivative and the dextran is between 1/99 and 30/70.

3. The prosthesis as claimed in claim 1 wherein said synthetic support is also impregnated with at least one covalently crosslinked natural or synthetic polysaccharide functionalized at least with carboxylate and/or sulfate functions.

4. The prosthesis as claimed in claim 3, wherein the weight ratio between the functionalized polysaccharide and the dextran is between 1/99 and 30/70.

5. The prosthesis as claimed in claim 3 wherein the weight ratio between the functionalized dextran derivative and the functionalized polysaccharide is between 1/99 and 99/1.

6. The flexible vascular prosthesis as claimed in claim 1 wherein said prosthesis is obtained by a process which comprises the following steps:
    (a) preparation of a solution of at least one dextran and of at least one functionalized dextran derivative.
    (b) impregnation of the synthetic support using this solution, and
    (c) crosslinking of said dextran and of said functionalized dextran derivative.

7. The flexible vascular prosthesis as claimed in claim 1 wherein said prosthesis is obtained by a process which comprises the following steps:
    (a) preparation of a solution of a least one dextran and of at least one functionalized dextran derivative,
    (b) impregnation of the synthetic support using this solution,
    (c) crosslinking of said dextran and of said functionalized dextran derivative,
    and which comprises, between steps (a) and (b), the addition of a crosslinking agent to the solution prepared during step (a).

8. The flexible vascular prosthesis as claimed in claim 1 wherein said prosthesis is obtained by a process which comprises the following steps:
    (a) preparation of a solution of at least one dextran and of at least one functionalized dextran derivative,
    (b) impregnation of the synthetic support using this solution,
    (c) crosslinking of said dextran and of said functionalized dextran derivative,
    and which comprises, between steps (b) and (c), a step of drying the support, followed by a step of impregnating the support with a solution, in at least one organic solvent, of a crosslinking agent.

9. The flexible vascular prosthesis as claimed in claim 1 wherein said prosthesis is obtained by a process which comprises the following steps:
    (a) preparation of a solution of at least one dextran and of at least one functionalized dextran derivative,
    (b) impregnation of the synthetic support using this solution,
    (c) crosslinking of said dextran and of said functionalized dextran derivative,
    and which comprises, between steps (b) and (c), a step of drying the support, followed by a step of impregnating the support with a solution, in at least one organic solvent, of a crosslinking agent,
    and wherein steps (b) and (c) are each carried out at a pH of between 3 and 10 and at a temperature of between 10 and 40° C., and step (b) is carried out for a time of less than or equal to 150 minutes and step (c) is carried out for a time of between 15 minutes and 18 hours.

10. The flexible vascular prosthesis as claimed in claim 1 wherein said prosthesis is obtained by a process which comprises the following steps:
    (a) preparation of a solution of at least one dextran and of at least one functionalized dextran derivative,
    (b) impregnation of the synthetic support using this solution,
    (b) crosslinking of said dextran and of said functionalized dextran derivative,
    wherein said solution of at least one dextran and of at least one functionalized dextran derivative prepared during step (a) also comprises at least one natural or synthetic polysaccharide functionalized at least with carboxylate and/or sulfate functions.

11. The flexible vascular prosthesis as claimed in claim 1 wherein said prosthesis is obtained by a process which comprises the following steps:
    (a) preparation of a solution of at least one dextran and of at least one functionalized dextran derivative,
    (b) impregnation of the synthetic support using this solution,
    (c) crosslinking of said dextran and of said functionalized dextran derivative,
    wherein said solution of at least one dextran and of at least functionalized dextran derivative prepared during step (a) also comprises at least one additive chosen from plasticizers and softeners and/or one or more active principles selected from the group consisting of anticoagulants, antibacterial agents and anti-infectious agents.

* * * * *